US010918682B2

(12) United States Patent
Lin et al.

(10) Patent No.: US 10,918,682 B2
(45) Date of Patent: Feb. 16, 2021

(54) METHOD OF ENHANCING THE GENE EXPRESSION LEVEL OF TGM1, KRT, AQP3, FLG, GBA, AND HAS USING PLANT EXTRACTS

(71) Applicant: TCI CO., LTD, Taipei (TW)

(72) Inventors: Yung-Hsiang Lin, Taipei (TW); I-Hui Chen, Taipei (TW); Kai-Wen Kan, Taipei (TW); Fu Chen Liu, Taipei (TW); Ciao-Ting Chen, Taipei (TW)

(73) Assignee: TCI CO., LTD., Taipei (TW)

( * ) Notice: Subject to any disclaimer, the term of this patent is extended or adjusted under 35 U.S.C. 154(b) by 11 days.

(21) Appl. No.: 16/499,436

(22) PCT Filed: Apr. 3, 2018

(86) PCT No.: PCT/CN2018/081720
§ 371 (c)(1),
(2) Date: Sep. 30, 2019

(87) PCT Pub. No.: WO2018/184527
PCT Pub. Date: Oct. 11, 2018

(65) Prior Publication Data
US 2020/0046792 A1 Feb. 13, 2020

Related U.S. Application Data

(63) Continuation of application No. 62/503,185, filed on May 8, 2017, which is a continuation of application No. 62/480,860, filed on Apr. 3, 2017.

(51) Int. Cl.
| | | |
|---|---|---|
| *A61K 36/00* | (2006.01) | |
| *A61K 36/185* | (2006.01) | |
| *A23L 33/105* | (2016.01) | |
| *A61K 9/00* | (2006.01) | |
| *A61K 9/08* | (2006.01) | |
| *A61K 9/48* | (2006.01) | |
| *A61P 3/04* | (2006.01) | |
| *A61K 31/01* | (2006.01) | |
| *A61K 31/015* | (2006.01) | |
| *A61K 36/21* | (2006.01) | |
| *A61K 36/258* | (2006.01) | |
| *A61K 36/31* | (2006.01) | |
| *A61K 36/45* | (2006.01) | |
| *A61K 36/48* | (2006.01) | |
| *A61K 36/53* | (2006.01) | |
| *A61K 36/67* | (2006.01) | |
| *A61K 36/73* | (2006.01) | |
| *A61K 36/74* | (2006.01) | |
| *A61K 36/752* | (2006.01) | |
| *A61K 36/815* | (2006.01) | |
| *A61K 36/82* | (2006.01) | |
| *A61K 36/87* | (2006.01) | |
| *A61K 36/886* | (2006.01) | |
| *A61K 36/8962* | (2006.01) | |
| *A61K 36/9066* | (2006.01) | |
| *A61K 8/9789* | (2017.01) | |
| *A61P 17/16* | (2006.01) | |
| *A61Q 19/00* | (2006.01) | |
| *A23F 3/16* | (2006.01) | |
| *A61K 8/97* | (2017.01) | |
| *A61Q 17/04* | (2006.01) | |
| *A61P 19/04* | (2006.01) | |
| *A61Q 19/08* | (2006.01) | |

(52) U.S. Cl.
CPC ............ *A61K 36/185* (2013.01); *A23F 3/163* (2013.01); *A23L 33/105* (2016.08); *A61K 8/97* (2013.01); *A61K 8/9789* (2017.08); *A61K 9/0056* (2013.01); *A61K 9/0095* (2013.01); *A61K 9/08* (2013.01); *A61K 9/48* (2013.01); *A61K 31/01* (2013.01); *A61K 31/015* (2013.01); *A61K 36/21* (2013.01); *A61K 36/258* (2013.01); *A61K 36/31* (2013.01); *A61K 36/45* (2013.01); *A61K 36/48* (2013.01); *A61K 36/53* (2013.01); *A61K 36/67* (2013.01); *A61K 36/73* (2013.01); *A61K 36/74* (2013.01); *A61K 36/752* (2013.01); *A61K 36/815* (2013.01); *A61K 36/82* (2013.01); *A61K 36/87* (2013.01); *A61K 36/886* (2013.01); *A61K 36/8962* (2013.01); *A61K 36/9066* (2013.01); *A61P 3/04* (2018.01); *A61P 17/16* (2018.01); *A61P 19/04* (2018.01); *A61Q 17/04* (2013.01); *A61Q 19/007* (2013.01); *A61Q 19/08* (2013.01); *A23V 2002/00* (2013.01)

(58) Field of Classification Search
CPC .................................................... A61K 36/00
USPC ........................................................ 424/725
See application file for complete search history.

(56) References Cited

FOREIGN PATENT DOCUMENTS

CN          102273529 A       12/2011

OTHER PUBLICATIONS

Yang, Yan et al., "Analysis of Use of α—Hydroxy Acid in Cosmetics", Chinese Journal of Health Laboratory Technology, 18(1), Jan. 10, 2008, p. 133-134.
Wu, Qianhu, "Cosmetic Food Encyclopedia", Oct. 31, 2013, p. 45.
(Continued)

*Primary Examiner* — Michael V Meller
(74) *Attorney, Agent, or Firm* — Chieh-Mei Wang

(57) ABSTRACT

The present invention provides a method of a composition containing plant extracts for enhancing the gene expression level of TGM1, KRT, AQP3, FLG, GBA, and HAS. Compared to a single plant extract, the combination of the plant extracts of the present invention can more effectively enhance the expression level of skin moisturizing genes. The plant extracts constituting the composition include: an extract of spinach, blueberry, Pu-erh tea, or Four Seasons Spring tea.

5 Claims, 1 Drawing Sheet
Specification includes a Sequence Listing.

(56) References Cited

OTHER PUBLICATIONS

Xu, Qing, "Dry Skin Relief in Winter", Dec. 28, 2011, p. 35, Hunan Agricultural Machinery.
Qi, Jicheng, "Development and Application Prospect of Plant Polyphenol", Jul. 15, 2007, p. 31-34, China Pharmaceutical Technology Exchange.

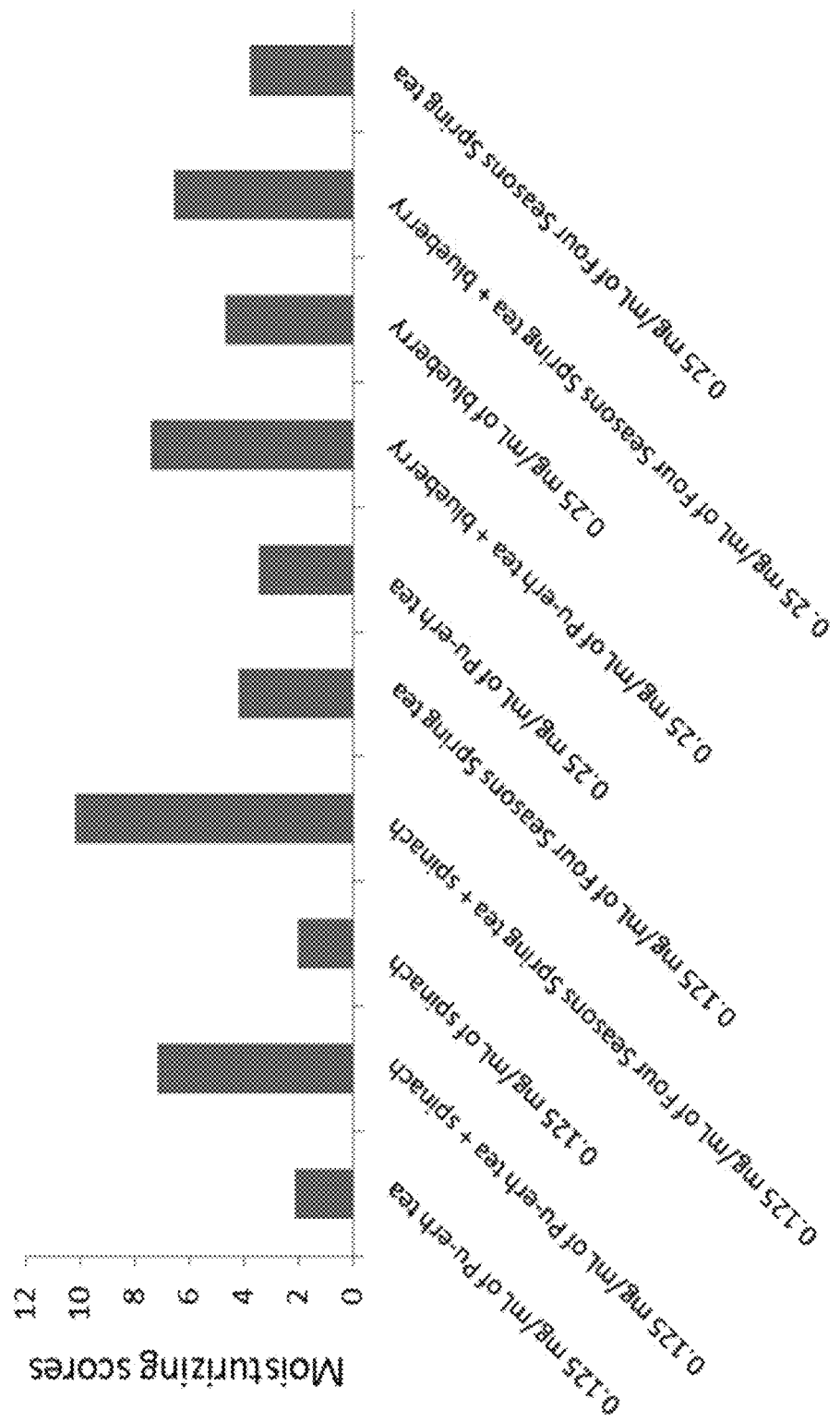

SEQUENCE LISTING

<160> NUMBER OF SEQ ID NOS: 20

<210> SEQ ID NO 1
<211> LENGTH: 22
<212> TYPE: DNA
<213> ORGANISM: Artificial sequence
<220> FEATURE:
<223> OTHER INFORMATION: PCR primer

<400> SEQUENCE: 1
gatcgcatca cccttgagtt ac                                    22

```
<210> SEQ ID NO 2
<211> LENGTH: 19
<212> TYPE: DNA
<213> ORGANISM: Artificial sequence
<220> FEATURE:
<223> OTHER INFORMATION: PCR primer

<400> SEQUENCE: 2
gcaggttcag attctgccc                                                    19

<210> SEQ ID NO 3
<211> LENGTH: 21
<212> TYPE: DNA
<213> ORGANISM: Artificial sequence
<220> FEATURE:
<223> OTHER INFORMATION: PCR primer

<400> SEQUENCE: 3
agagtggacc aactgaagag t                                                 21

<210> SEQ ID NO 4
<211> LENGTH: 21
<212> TYPE: DNA
<213> ORGANISM: Artificial sequence
<220> FEATURE:
<223> OTHER INFORMATION: PCR primer

<400> SEQUENCE: 4
attctctgca tttgtccgct t                                                 21

<210> SEQ ID NO 5
<211> LENGTH: 22
<212> TYPE: DNA
<213> ORGANISM: Artificial sequence
<220> FEATURE:
<223> OTHER INFORMATION: PCR primer

<400> SEQUENCE: 5
tcctacttgg acaaagttcg gg                                                22

<210> SEQ ID NO 6
<211> LENGTH: 19
<212> TYPE: DNA
<213> ORGANISM: Artificial sequence
<220> FEATURE:
<223> OTHER INFORMATION: PCR primer

<400> SEQUENCE: 6
cccctgatgt gagttgcca                                                    19

<210> SEQ ID NO 7
<211> LENGTH: 20
<212> TYPE: DNA
<213> ORGANISM: Artificial sequence
<220> FEATURE:
<223> OTHER INFORMATION: PCR primer

<400> SEQUENCE: 7
ttctgaacga gatgcgtgac                                                   20

<210> SEQ ID NO 8
<211> LENGTH: 20
<212> TYPE: DNA
<213> ORGANISM: Artificial sequence
<220> FEATURE:
<223> OTHER INFORMATION: PCR primer
```

<400> SEQUENCE: 8
gcagctcaat ctccaggttc                                          20

<210> SEQ ID NO 9
<211> LENGTH: 19
<212> TYPE: DNA
<213> ORGANISM: Artificial sequence
<220> FEATURE:
<223> OTHER INFORMATION: PCR primer

<400> SEQUENCE: 9
ggggagatgc tccacatcc                                           19

<210> SEQ ID NO 10
<211> LENGTH: 21
<212> TYPE: DNA
<213> ORGANISM: Artificial sequence
<220> FEATURE:
<223> OTHER INFORMATION: PCR primer

<400> SEQUENCE: 10
aaaggccagg ttgatggtga g                                        21

<210> SEQ ID NO 11
<211> LENGTH: 20
<212> TYPE: DNA
<213> ORGANISM: Artificial sequence
<220> FEATURE:
<223> OTHER INFORMATION: PCR primer

<400> SEQUENCE: 11
ggcaaatcct gaagaatcca                                          20

<210> SEQ ID NO 12
<211> LENGTH: 20
<212> TYPE: DNA
<213> ORGANISM: Artificial sequence
<220> FEATURE:
<223> OTHER INFORMATION: PCR primer

<400> SEQUENCE: 12
tgctttctgt gcttgtgtcc                                          20

<210> SEQ ID NO 13
<211> LENGTH: 20
<212> TYPE: DNA
<213> ORGANISM: Artificial sequence
<220> FEATURE:
<223> OTHER INFORMATION: PCR primer

<400> SEQUENCE: 13
tccagttgca caacttcagc                                          20

<210> SEQ ID NO 14
<211> LENGTH: 20
<212> TYPE: DNA
<213> ORGANISM: Artificial sequence
<220> FEATURE:
<223> OTHER INFORMATION: PCR primer

<400> SEQUENCE: 14
ttgtgctcag cataggcatc                                          20

<210> SEQ ID NO 15
<211> LENGTH: 23

```
<212> TYPE: DNA
<213> ORGANISM: Artificial sequence
<220> FEATURE:
<223> OTHER INFORMATION: PCR primer

<400> SEQUENCE: 15
aagaacaact tccacgaaaa ggg                                    23

<210> SEQ ID NO 16
<211> LENGTH: 20
<212> TYPE: DNA
<213> ORGANISM: Artificial sequence
<220> FEATURE:
<223> OTHER INFORMATION: PCR primer

<400> SEQUENCE: 16
ggctgggtca agcatagtgt                                        20

<210> SEQ ID NO 17
<211> LENGTH: 19
<212> TYPE: DNA
<213> ORGANISM: Artificial sequence
<220> FEATURE:
<223> OTHER INFORMATION: PCR primer

<400> SEQUENCE: 17
cgcagcaact tccatgagg                                         19

<210> SEQ ID NO 18
<211> LENGTH: 21
<212> TYPE: DNA
<213> ORGANISM: Artificial sequence
<220> FEATURE:
<223> OTHER INFORMATION: PCR primer

<400> SEQUENCE: 18
agtcgcacac ctggatgtag t                                      21

<210> SEQ ID NO 19
<211> LENGTH: 21
<212> TYPE: DNA
<213> ORGANISM: Artificial sequence
<220> FEATURE:
<223> OTHER INFORMATION: PCR primer

<400> SEQUENCE: 19
catgtacgtt gctatccagg c                                      21

<210> SEQ ID NO 20
<211> LENGTH: 21
<212> TYPE: DNA
<213> ORGANISM: Artificial sequence
<220> FEATURE:
<223> OTHER INFORMATION: PCR primer

<400> SEQUENCE: 20
ctccttaatg tcacgcacga t                                      21
```

METHOD OF ENHANCING THE GENE EXPRESSION LEVEL OF TGM1, KRT, AQP3, FLG, GBA, AND HAS USING PLANT EXTRACTS

CROSS-REFERENCE TO RELATED APPLICATION

This application claims priority of U.S. application No. 62/480,860, filed on Apr. 3, 2017 and U.S. application No. 62/503,185, filed on May 8, 2017 the content of which are incorporated herein in its entirety by references.

BACKGROUND OF THE INVENTION

1. Field of the Invention

The present invention relates to a composition containing plant extracts and the use thereof, and more particularly to the use of the composition containing plant extracts for enhancing the gene expression level of TGM1, KRT, AQP3, FLG, GBA, and HAS.

2. The Prior Art

The epidermis layer is the outermost layer of the skin, and is consisted of the stratum corneum, the granular layer, the spinous layer, and the basal layer are sequentially arranged from the outside to the inside. The epidermal layer is mainly formed by the differentiation of undifferentiated cylindrical keratinocytes in the basal layer and the process is called keratinization. The water content in keratinocytes is high, and as the cells metabolize and differentiate, the shape of keratinocytes will gradually become flat, and the nucleus and organelles will begin to degenerate and shrink, and dead cells without nucleus and organelles will be formed in the stratum corneum. The main function of the epidermis layer is to maintain the moisturizing of the skin and form a skin barrier to resist various external injuries. The outermost layer of the epidermis layer is composed of a weakly acidic sebum membrane and a stratum corneum such as a brick wall structure, which can lock the moisture and oil of the skin, resist the invasion of skin surface bacteria, and resist external foreign objects and ultraviolet light, which has a very important protective effect on the human body.

In the stratum corneum of the epidermis layer, although the keratinocytes are dead cells, the main component is keratin, which can absorb moisture to keep the skin moist, and keratinocytes also secrete substances such as hyaluronic acid as interstitial cells to maintain the structural integrity of the epidermal skin barrier to prevent water loss of the skin and form a complete protection. When the skin is exposed to excessive cold or hot conditions and ultraviolet light, it will make the keratinocytes cannot maintain the normal metabolic loops and damage the epidermal barrier of the skin, and then lead the skin to be rough, dry and desquamate, fragile and susceptible to irritation, sensitive redness, and also reduce the moisturizing ability of the skin, so the health of the stratum corneum is very important for moisturizing the skin and resisting external damage.

In summary, in order to solve the problem of the fragile, the sensitive, and the reduce the moisturizing ability of the skin caused by the damage of the stratum corneum, it is necessary to develop a composition that can effectively maintain the keratinocyte arrangement, maintain the integrity of the stratum corneum, and allow the keratinocytes to secrete more moisturizing factors to enhance the barrier and the moisturizing function of the skin.

However, the ingredients or drugs currently used for this purpose are limited. If it is a certain plant extract, it must be administered at a relatively high dose, and thus there are limitations in the cost of use and effect. Therefore, if a composition containing plurality of plant extracts with a small amount of each component can be administered to produce the similar effect when administered a high-dose of a single component, the use of the aforementioned effects can be greatly improved, and at the same time, the use cost can be reduced.

SUMMARY OF THE INVENTION

To solve the foregoing problem, one objective of the present invention is to provide a method of enhancing expression of transglutaminase 1 (TGM1), keratin (KRT), aquaporin 3 (AQP3), filaggrin (FLG), glucocerebrosidase (GBA), and hyaluronic synthase (HAS) genes, comprising administering to a subject in need thereof a composition comprising an effective amount of a plant extract; wherein the plant extract comprises at least one combination selected from the group consisting of a Pu-erh tea extract and a blueberry extract, a Pu-erh tea extract and a spinach extract, a Four Seasons Spring tea extract and a blueberry extract, and a Four Seasons Spring tea extract and a spinach extract.

In one embodiment of the present invention, the KRT gene comprises keratin 1 (KRT1), keratin 10 (KRT10), and keratin 14 (KRT14); the HAS gene comprises hyaluronic synthase 2 (HAS2) and hyaluronic synthase 3 (HAS3).

In one embodiment of the present invention, the plant extract comprises at least 0.125 mg/mL of the Pu-erh tea extract and at least 0.125 mg/mL of the spinach extract, at least 0.125 mg/mL of the Four Seasons Spring tea extract and at least 0.125 mg/mL of the spinach extract, at least 0.25 mg/mL of the Pu-erh tea extract and at least 0.25 mg/mL of the blueberry extract, or at least 0.25 mg/mL of the Pu-erh tea extract and at least 0.25 mg/mL of the Four Seasons Spring tea extract.

In one embodiment of the present invention, the composition promotes skin moisturization.

In one embodiment of the present invention, the composition further comprises a pharmaceutical acceptable carrier, and the composition is in a form of powder, granule, liquid, gel, or paste, and the composition is prepared in a form of a medicament or a food product.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

FIG. 1 is a diagram showing the moisturizing scores of different plant extracts or combinations.

DETAILED DESCRIPTION OF THE PREFERRED EMBODIMENT

The embodiments of the present invention are further described with the following drawings. The following embodiments are given to illustrate the present invention and are not intended to limit the scope of the present invention, and those having ordinary skill in the art can make some modifications and refinements without departing from the spirit and scope of the present invention. Therefore, the scope of the present invention is defined by the scope of the appended claims.

Definition

As used herein, the data provided represent experimental values that can vary within a range of ±20%, preferably within ±10%, and most preferably within ±5%.

EXAMPLE 1

Preparation of Each Plant Extract 1-1 Preparation of Four Seasons Spring Tea Extract The Four Seasons Spring tea extract was prepared as follows: first, the leaves of Four Seasons Spring tea plant were washed and dried, and then Four Seasons Spring was coarsely crushed by a pulverizer to be a crude material. The crude material of Four Seasons Spring tea was extracted using water as the solvent. The weight ratio of the solvent to the crude material was 5-20:1-5. The extraction temperature was at 50-100° C., preferably 75-95° C., for 0.5-3 hours to obtain the crude extract of the Four Seasons Spring tea. After the extraction, the crude extraction was cooled to room temperature. The crude extraction was filtered through a 400 mesh filter to remove residual solids. Furthermore, the filtered of the Four Seasons Spring tea was further concentrated under reduced pressure at 45-70° C. to obtain a concentrated product and the concentrated product was the Four Seasons Spring tea extract of the present invention.

1-2 Preparation of Spinach Extract

The spinach extract was obtained by extracting spinach (*Spinacia oleracea*), and the spinach extract used in the example was purchased from HONHSIANG farm products factory.

1-3 Preparation of Blueberry Extract

The blueberry extract was obtained by extracting the fruits of *Vaccinium cyanococcus*, and the blueberry extract used in the example was purchased from BIOMED HERBAL RESEARCH CO., LTD.

1-4 Preparation of Pu-erh Tea Extract

The Pu-erh tea extract was obtained by extracting the post-fermented leaves of *Camellia sinensis*, and the Pu-erh tea extract used in the example was purchased from Nanjing Zelang Biotechnology Co., Ltd.

EXAMPLE 2

Effects of Combination of the Plant Extracts on Enhancing the Gene Expression Level of TGM1, KRT, AQP3, FLG, GBA, and HAS The present invention performed the genetic analysis of TGM1, KRT, AQP3, FLG, GBA, and HAS by human primary epidermal keratinocytes (HPEK). The human primary epidermal keratinocytes were purchased from CELLnTEC (Switzerland) No. HPEK-50, and the cells were cultured in serum-free keratinocyte-SFM (Gibco, Inc., #10724-011, USA).

First, $1.5 \times 10^5$ of HPEK were seeded in 6-well culture plates containing 2 mL of the above culture medium, and the cells were divided into the following 10 groups with: (1) 0.125 mg/mL of the Pu-erh tea extract, (2) 0.125 mg/mL of the spinach extract, (3) 0.125 mg/mL of the Four Seasons Spring tea extract, (4) 0.125 mg/mL of the combination of the Pu-erh tea extract and the spinach extract mixed in a ratio of 1:1, (5) 0.125 mg/mL of the combination of the Four Seasons Spring tea extract and the spinach extract mixed in a ratio of 1:1, (6) 0.25 mg/mL of the Pu-erh tea extract, (7) 0.25 mg/mL of the blueberry extract, (8) 0.25 mg/mL of the Four Seasons Spring tea extract, (9) 0.25 mg/mL of the combination of the Pu-erh tea extract and the blueberry extract mixed in a ratio of 1:1, and (10) 0.25 mg/mL of the combination of the Four Seasons Spring tea extract and the blueberry extract mixed in a ratio of 1:1; wherein, the cells treated without any extract was as the blank control group. After added the plant extracts of the above groups, the cells were stimulated by each group of the plant extracts at 37° C. The culture medium of each group was changed with fresh one added with each group of the specific plant extracts after 6 and 24 hours of culture respectively. Next, cells were lysis with lysis buffer, and then the total RNAs of cells were collected from the each of the ten groups by the RNA extraction kit (purchased from Geneaid, Taiwan, Lot No. FC24015-G). Then, 2000 ng of extracted RNAs was subjected as the template to reverse transcription into the corresponding cDNA products of the specific mRNAs with SuperScript® III reverse transcriptase (purchased from Invitrogene, USA, number 18080-051). Then, the cDNA products of these 10 groups were used as template and mixed with the primers of the target gene in Table 1 and the mRNA expression level of TGM1, KRT1, KRT10, KRT14, AQP3, FLG, GBA, HAS2, and HAS3 of each group were quantified by quantitative real-time polymerase chain reaction (qPCR) with ABI StepOnePlus™ Real-Time PCR System (Thermo Fisher Scientific, USA) and KAPA SYBR® FAST qPCR Kits (purchased from Sigma, USA, No. 38220000000), wherein the PCR conditions were performed as described below: 40 PCR cycles of 95° C. for 1 sec and 60° C. for 20 secs. Wherein, the quantitative value was taken from the cycle threshold (Ct), and the relative amount of mRNA of the target gene was derived from Equation $2^{-\Delta Ct}$, wherein $\Delta Ct = Ct_{target\ gene} - Ct_{ACTB}$ (β-actin). Then, the SCORE method was used to quantify the scores of each gene expression levels in the above ten groups. The scores of each gene was summed as the moisturizing scores of each group, wherein the SCORE method was calculated using the loop threshold of the ACTB gene and the reference gene (the corresponding gene in the blank control group).

TABLE 1

The sequence of the PCR primer

| Gene | Primer | Number | Primer length (ntds) |
|---|---|---|---|
| TGM1 | TGM1-F | SEQ ID NO: 1 | 22 |
| | TGM1-R | SEQ ID NO: 2 | 19 |
| KRT1 | KRT1-F | SEQ ID NO: 3 | 21 |
| | KRT1-R | SEQ ID NO: 4 | 21 |
| KRT10 | KRT10-F | SEQ ID NO: 5 | 22 |
| | KRT10-R | SEQ ID NO: 6 | 19 |
| KRT14 | KRT14-F | SEQ ID NO: 7 | 20 |
| | KRT14-R | SEQ ID NO: 8 | 20 |
| AQP3 | AQP3-F | SEQ ID NO: 9 | 19 |
| | AQP3-R | SEQ ID NO: 10 | 21 |
| FLG | FLG-F | SEQ ID NO: 11 | 20 |
| | FLG-R | SEQ ID NO: 12 | 20 |
| GBA | GBA-F | SEQ ID NO: 13 | 20 |
| | GBA-R | SEQ ID NO: 14 | 20 |
| HAS2 | HAS2-F | SEQ ID NO: 15 | 23 |
| | HAS2-R | SEQ ID NO: 16 | 20 |
| HAS3 | HAS3-F | SEQ ID NO: 17 | 19 |
| | HAS3-R | SEQ ID NO: 18 | 21 |
| β-actin | ACTB-F | SEQ ID NO: 19 | 21 |
| | ACTB-R | SEQ ID NO: 20 | 21 |

The moisturizing scores of each combination of the plant extracts of the present invention was shown in Table 2 and FIG. 1; wherein, the higher the moisturizing scores, the better the promotion of the skin moisturization. Previous studies have indicated that transglutaminase 1 (TGM) forms a strong bond between the cell membrane of keratinocytes and structural proteins, and then increases the strength and stability of the epidermal layer; keratin (KRT) forms keratin microfilaments, and filaggrin (FLG) helps keratin microfilaments assemble into a strong network that provides strength and elasticity to the skin; aquaporin (AQP) increases the permeability of water in keratinocytes to increase the water content of keratinocytes; hyaluronic synthase (HAS) promotes the ability of keratinocytes to secrete hyaluronic acid, and then makes the structure of the stratum corneum intact and enhances the skin barrier function, which can make the skin retain moisturizing; and Glucocerebrosidase (GBA) is associated with integrity maintaining the structure of keratinous. The moisturizing scores obtained by treating keratinocytes with 0.125 mg/mL of the Pu-erh tea extract, the Four Seasons Spring tea extract, and the spinach extract alone were 2.16, 4.2, and 2.04, respectively. However, the moisturizing scores obtained by treating keratinocytes with 0.125 mg/mL of the combination of the Pu-erh tea extract and the spinach extract mixed in a ratio of 1:1; and with 0.125 mg/mL of the combination of the Four Seasons Spring tea extract and the spinach extract mixed in a ratio of 1:1 were 7.2 and 10.2, respectively; the moisturizing scores obtained by treating keratinocytes with 0.25 mg/mL of the Pu-erh tea extract, the Four Seasons Spring tea extract, the blueberry extract were 3.5, 3.8, and 4.7, respectively; however, the moisturizing scores obtained by treating keratinocytes with 0.25 mg/mL of the combination of the Pu-erh tea extract and the blueberry extract mixed in a ratio of 1:1; and with 0.25 mg/mL of the combination of the Four Seasons Spring tea extract and the blueberry extract mixed in a ratio of 1:1 were 7.4 and 6.6, respectively. The results indicate that the composition comprising a combination of the Pu-erh tea extract and the blueberry extract, the Pu-erh tea extract and the spinach extract, the Four Seasons Spring tea extract and the blueberry extract, or the Four Seasons Spring tea extract and the spinach extract was quite effective in enhancing the expression of the skin moisturizing genes, and could more effectively enhance the gene expression level of TGM1, KRT1, KRT10, KRT14, AQP3, FLG, GBA, HAS2, and HAS3 than the Pu-erh tea extract alone, the Four Seasons Spring tea extract alone, the spinach extract alone, and the blueberry extract alone to more effectively maintain the keratinocyte arrangement of the skin, make the stratum corneum layer structure intact, enhance the skin barrier function, and make the skin produce more moisturizing factors.

TABLE 2

The moisturizing scores of the expression of the skin moisturization-related genes calculated for each group

| Plant extracts/ Combinations | Concentration/Ratio | Moisturizing scores |
|---|---|---|
| Pu-erh tea | 0.125 mg/mL | 2.16 |
| Pu-erh tea + Spinach | 0.125 mg/mL (1:1) | 7.2 |
| Spinach | 0.125 mg/mL | 2.04 |
| Four Seasons Spring tea + Spinach | 0.125 mg/mL (1:1) | 10.2 |
| Four Seasons Spring tea | 0.125 mg/mL | 4.2 |
| Pu-erh tea | 0.25 mg/mL | 3.5 |
| Pu-erh tea + Blueberry | 0.25 mg/mL (1:1) | 7.4 |
| Blueberry | 0.25 mg/mL | 4.7 |
| Four Seasons Spring tea + Blueberry | 0.25 mg/mL (1:1) | 6.6 |
| Four Seasons Spring tea | 0.25 mg/mL | 3.8 |

In summary, the composition of the present invention containing a combination of the Pu-erh tea extract and the blueberry extract, the Pu-erh tea extract and the spinach extract, the Four Seasons Spring tea extract and the blueberry extract, or the Four Seasons Spring tea extract and the spinach extract can produce an unexpected multiplication effect that can significantly enhance the expression level of the skin moisturizing genes compared with the Pu-erh tea extract alone or the Four Seasons Spring tea extract alone to more effectively maintain the keratinocyte arrangement of the skin, make the stratum corneum layer structure intact, enhance the skin barrier function, and make the skin produce more moisturizing factors.

Furthermore, the composition containing plant extracts of the present invention for enhancing a gene expression level of transglutaminase 1, keratin, aquaporin 3, filaggrin, glucocerebrosidase, and hyaluronic synthase can be further added to a food, a health food, a dietary supplement, or a drink. Besides, the composition of the present invention can be prepared to be a pharmaceutical composition, and the pharmaceutical composition can be further added to a carrier or other adjuvant well known in the art. The dosage form of the pharmaceutical composition can be, but is not limited to, a solution, a capsule, or a lozenge.

What is claimed is:

1. A method of treating human skin in need of moisturization in a human in need thereof consisting essentially of administering to the human in need thereof therapeutically effective amounts of an extract selected from the group consisting of Pu-erh extract and Four seasons spring tea extract, and an extract selected from the group consisting of spinach extract and blueberry extract.

2. The method of claim 1, wherein the therapeutically effective amounts of the Pu-erh tea extract and the spinach extract are at least 0.125 mg/mL.

3. The method of claim 1, wherein the therapeutically effective amounts of the Four Seasons Spring tea extract and the spinach extract are at least 0.125 mg/mL.

4. The method of claim 1, wherein the therapeutically effective amounts of the Pu-erh tea extract and the blueberry extract are at least 0.25 mg/mL.

5. The method of claim 1, wherein the therapeutically effective amounts of the Pu-erh tea extract and the Four Seasons Spring tea extract are at least 0.25 mg/mL.

* * * * *